(12) United States Patent
Chen et al.

(10) Patent No.: US 11,941,732 B2
(45) Date of Patent: Mar. 26, 2024

(54) MULTI-SLICE MRI DATA PROCESSING USING DEEP LEARNING TECHNIQUES

(71) Applicant: Shanghai United Imaging Intelligence Co., Ltd., Shanghai (CN)

(72) Inventors: Xiao Chen, Lexington, MA (US); Zhang Chen, Brookline, MA (US); Shanhui Sun, Lexington, MA (US); Terrence Chen, Lexington, MA (US)

(73) Assignee: Shanghai United Imaging Intelligence Co., Ltd., Shanghai (CN)

( * ) Notice: Subject to any disclaimer, the term of this patent is extended or adjusted under 35 U.S.C. 154(b) by 345 days.

(21) Appl. No.: 17/513,320

(22) Filed: Oct. 28, 2021

(65) Prior Publication Data

US 2023/0135995 A1 May 4, 2023

(51) Int. Cl.
G06T 11/00 (2006.01)
A61B 5/00 (2006.01)
A61B 5/055 (2006.01)
G06T 7/00 (2017.01)

(52) U.S. Cl.
CPC ............ *G06T 11/008* (2013.01); *A61B 5/055* (2013.01); *A61B 5/7267* (2013.01); *G06T 7/0012* (2013.01); *G06T 2207/10088* (2013.01); *G06T 2207/20081* (2013.01); *G06T 2207/20084* (2013.01); *G06T 2207/30016* (2013.01); *G06T 2207/30048* (2013.01)

(58) Field of Classification Search
CPC ................. G06T 11/008; G06T 7/0012; G06T 2207/10088; G06T 2207/20081; G06T 2207/20084; G06T 2207/30016; G06T 2207/30048; A61B 5/055; A61B 5/7267; A61B 5/7203; A61B 5/7257; A61B 2576/023; A61B 2576/026; G06N 3/08; G06V 10/774; G06V 10/82
See application file for complete search history.

(56) References Cited

U.S. PATENT DOCUMENTS

2021/0217213 A1* 7/2021 Cole ...................... G06N 3/088

* cited by examiner

*Primary Examiner* — Christopher Wait
(74) *Attorney, Agent, or Firm* — Zhong Law LLC (57) ABSTRACT

Disclosed herein are systems, methods, and instrumentalities associated with reconstructing magnetic resonance (MR) images based on multi-slice, under-sampled MRI data (e.g., k-space data). The multi-slice MRI data may be acquired using a simultaneous multi-slice (SMS) technique and MRI information associated with multiple MRI slices may be entangled in the multi-slice MRI data. A neural network may be trained and used to disentangle the MRI information and reconstruct MRI images for the different slices. A data consistency component may be used to estimate k-space data based on estimates made by the neural network, from which respective MRI images associated with multiple MRI slices may be obtained by applying a Fourier transform to the k-space data.

20 Claims, 6 Drawing Sheets

MULTI-SLICE MRI DATA PROCESSING USING DEEP LEARNING TECHNIQUES

BACKGROUND

Magnetic resonance imaging (MRI) techniques may be used to collect data in a spatial-frequency space (e.g., commonly referred to as k-space) and images generated based on the collected data may provide insights about the characteristics of an anatomical structure that are important to clinical studies and diagnoses. The collection of k-space data may be a slow process and, as such, under-sampling may be applied to accelerate the operation. The under-sampled k-space data may then be reconstructed (e.g., into an MRI image) to obtain results having a similar quality as a fully-sampled dataset (e.g., a fully-sample MRI image). Conventional MRI acceleration techniques such as compressed sensing (CS) and parallel imaging (PI) may require good coil configurations (e.g., where multiple coils have discriminative powers) and/or iterative calculations, rendering them unsuitable or unsatisfactory for certain use cases such as those involving multi-slice data collection (e.g., simultaneous multi-slice data collections). Accordingly, systems, methods, and instrumentalities are highly desirable for reconstructing under-sampled MRI information (e.g., k-space data and/or MR images) and doing so in a manner that meets the real requirements and limits of clinical practices.

SUMMARY

Described herein are systems, methods, and instrumentalities associated with reconstructing magnetic resonance imaging (MRI) images based on a simultaneous multi-slice (e.g., two or more) dataset comprising under-sampled MRI data (e.g., MRI imagery or k-space data). Such an SMS dataset may include multiple MRI slices that are acquired (e.g., excited) simultaneously during an MRI scan procedure. For example, the SMS dataset may include first under-sampled MRI data associated with a first MRI slice, second under-sampled MRI data associated with a second MRI slice, etc. In accordance with one or more embodiments described herein, an artificial neural network (ANN) may be trained and used to obtain (e.g., receive) the SMS dataset and generate a first reconstructed MRI image corresponding to the first MRI slice and a second reconstructed MRI image corresponding to the second MRI slice. The ANN may be trained to perform these tasks through a training process that may include processing first under-sampled MRI training data of an SMS training dataset through an instance of the ANN to obtain a first estimated MRI image and processing second under-sampled MRI training data of the SMS training dataset through the instance of the ANN to obtain a second estimated MRI image, where the first and second under-sampled MRI training data may correspond to a first MRI slice and a second MRI slice of the SMS training dataset, respectively. The training may further include determining a combined training loss (e.g., such as an average loss, a triplet loss, etc.) by jointly considering a first training loss associated with the first estimated MRI image and a second training loss associated with the second estimated MRI image, and adjusting parameters of the instance of the ANN based on a gradient descent of the combined training loss.

In examples, the first under-sampled MRI data may include first artifacts that are associated with the second under-sampled MRI data, the second under-sampled MRI data may include second artifacts that are associated with the first under-sampled MRI data, but the first reconstructed MRI image and the second reconstructed MRI image may be substantially free of the first artifacts and the second artifacts, respectively. The first reconstructed MRI image and the second reconstructed MRI image may also have a quality (e.g., resolution) substantially similar to that of a fully-sampled MRI image. In examples, the ANN described herein may include a first sub-network and a second sub-network that share substantially similar structures and operating parameters. The first sub-network may be configured to process the first under-sampled MRI data and the second sub-network may be configured to process the second under-sampled MRI data. During training of the ANN, the first sub-network (e.g., of the instance of the ANN used for training) may be configured to process the first under-sampled MRI training data, the second sub-network (e.g., of the instance of the ANN used for training) may be configured to process the second under-sampled MRI training data, and mirrored updates may be applied to respective parameters of the first sub-network and the second sub-network based on the training loss described herein.

In examples, the ANN described herein may further comprise a data consistency (DC) component configured to estimate k-space data based on a first intermediate image generated by the ANN using the first under-sampled MRI data and a second intermediate image generated by the ANN using the second under-sampled MRI data. The first reconstructed MRI image and the second reconstructed MRI image may then be generated by applying an inverse Fourier transform (e.g., a 3D fast Fourier transform (FFT)) to the estimated k-space data. In examples, prior to applying the inverse Fourier transform to the estimated k-space data, at least a portion of the estimated k-space data may be replaced with a corresponding portion of the SMS dataset.

In examples, the first under-sampled MRI data comprised in the SMS dataset may include MRI data that are acquired using a first set of one or more coils. The second under-sampled MRI data comprised in the SMS dataset may include MRI data acquired using a second set of one or more coils. In these examples, respective coil sensitivity maps associated with the first set of one or more coils and the second set of one or more coils may be determined and used to estimate the k-space data described above.

BRIEF DESCRIPTION OF THE DRAWINGS

A more detailed understanding of the examples disclosed herein may be obtained from the following description, given by way of example in conjunction with the accompanying drawing.

DETAILED DESCRIPTION

The present disclosure is illustrated by way of example, and not by way of limitation, in the figures of the accompanying drawings.

Figure 1:
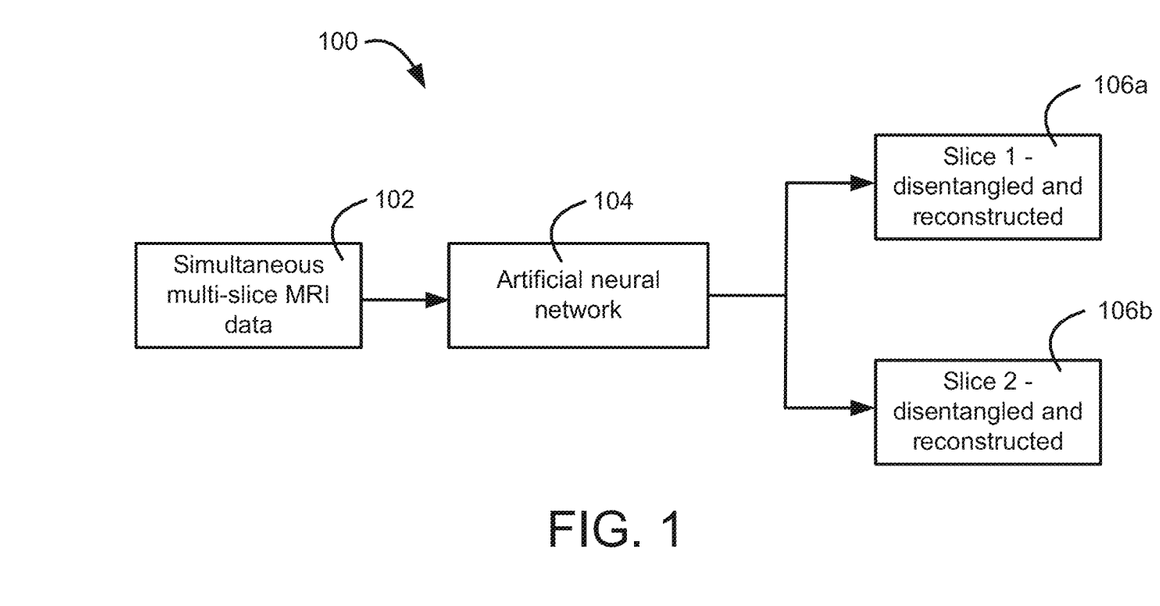
FIG. 1 is a block diagram illustrating an example system for processing an under-sampled simultaneous multi-slice (SMS) dataset.

FIG. 1 is a block diagram illustrating an example system 100 for processing a simultaneous multi-slice (SMS) dataset 102 collected by a magnetic resonance imaging (MRI) device (e.g., an MRI scanner). The SMS dataset 102 may include under-sampled MRI information associated with multiple MRI slices (e.g., two or more MRI slices including a first MRI slice and a second MRI slice) of an anatomical structure. The anatomical structure may be, for example, the human heart or the human brain, and the multiple MRI slices of the anatomical structure may be acquired simultaneously by the MRI device during a scan procedure (e.g., using a simultaneous multi-slice (SMS) excitation technique). The SMS dataset 102 may include different types of data or information. For example, the SMS dataset 102 may include under-sampled k-space data (e.g., raw MRI data) that indicates the frequency, phase, and/or intensity of the signals captured by the MRI device during a scan procedure. Such under-sampled k-space data may be characterized by a Cartesian or non-Cartesian trajectory, and/or may be collected using a uniform, random, or pseudo-random under-sampling technique. The SMS dataset 102 may also include imagery data (e.g., one or more MRI images) that visually depicts the anatomical structure based on the k-space data collected by the MRI device. These images may include a single static image or multiple dynamic images (e.g., multi-contrast images) that may be derived, for example, by applying a Fourier transform (e.g., inverse fast Fourier transform (FFT)) to the collected k-space data. In examples, the under-sampled MRI information associated with the multiple MRI slices may be entangled in the SMS dataset 102 (e.g., multiple slices may overlap in the image(s) included in the SMS dataset 102, one slice may include artifacts associated with another slice, etc.). Further, since the multiple slices may be separated in space, there may also be a discontinuity among the MRI slice information included in the SMS dataset 102.

The system 100 shown in FIG. 1 may include an artificial neural network (ANN) 102 configured (e.g., trained) to remove noises (e.g., artifacts) from the SMS dataset 102 and/or disentangle the multiple slices included in the SMS dataset 102. For example, the ANN 104 may be pre-trained to denoise the SMS dataset 102 (e.g., by learning the similarities and/or dissimilarities of the multiple slices included in the dataset), reconstruct the denoised multi-slice MRI data in a k-space, and derive respective reconstructed MRI data 106a, 106b (e.g., MRI images) corresponding to the multiple slices. Each of the reconstructed MRI data 106a and 106b may be substantially free of the artifacts introduced by other MRI slice(s) and, as such, may be disentangled from other MRI slice(s). The reconstructed MRI data 106a and 106b may also have a quality (e.g., resolution) similar to that of full-sampled MRI data (e.g., full-sampled MRI images). As will be described in greater detail below, the ANN 104 may include component(s) associated with decreasing the noise level in the reconstructed MRI data, component(s) associated with compensating for an estimation/prediction bias, and component(s) for incorporating other acceleration techniques into the disentanglement/reconstruction process.

Figure 2:
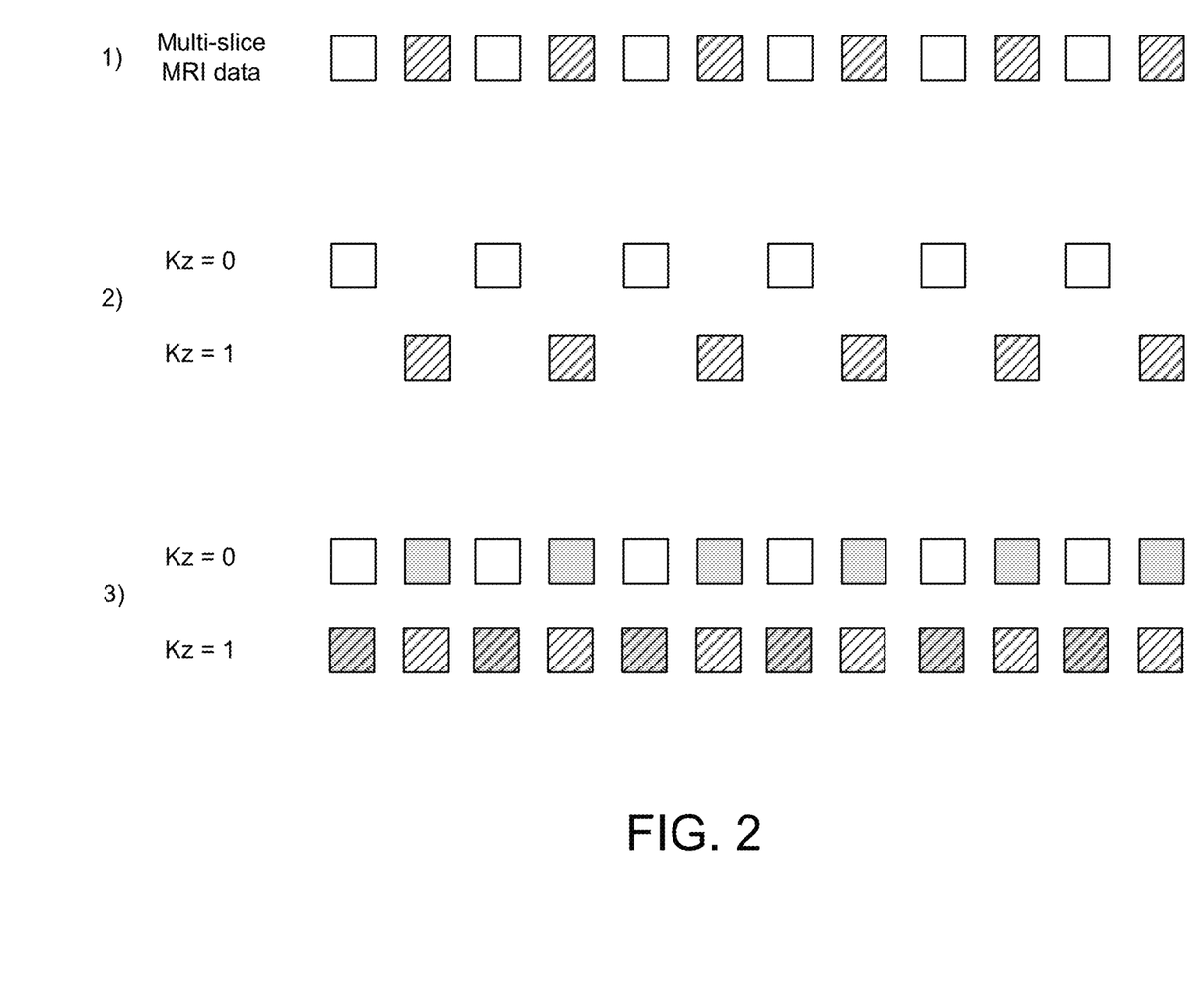
FIG. 2 is a block diagram illustrating example operations that may be associated with multi-slice MRI data processing.

FIG. 2 illustrates example operations that may be performed by a multi-slice MRI data processing system (e.g., the system 100 of FIG. 1) in accordance with one or more embodiments described herein. As shown, the data processing system may obtain (e.g., receive) an MRI dataset that includes under-sampled MRI data associated with multiple MRI slices (e.g., simultaneously acquired MRI data Kz=0 and MRI data Kz=1 that may correspond to respective phase encodings along a slice direction). In the simultaneously acquired multi-slice MRI dataset, respective data associated with the multiple slices may be entangled (e.g. as shown in 1)), and the data processing system described herein may be configured to, using an artificial neural network (e.g., pre-trained to learn a multi-slice MRI data processing model), disentangle the data associated with the multiple slices (e.g., at 2)) and reconstruct the data (e.g., at 3)) to a higher quality (e.g., similar to that of a fully-sampled MRI dataset).

Figure 3:
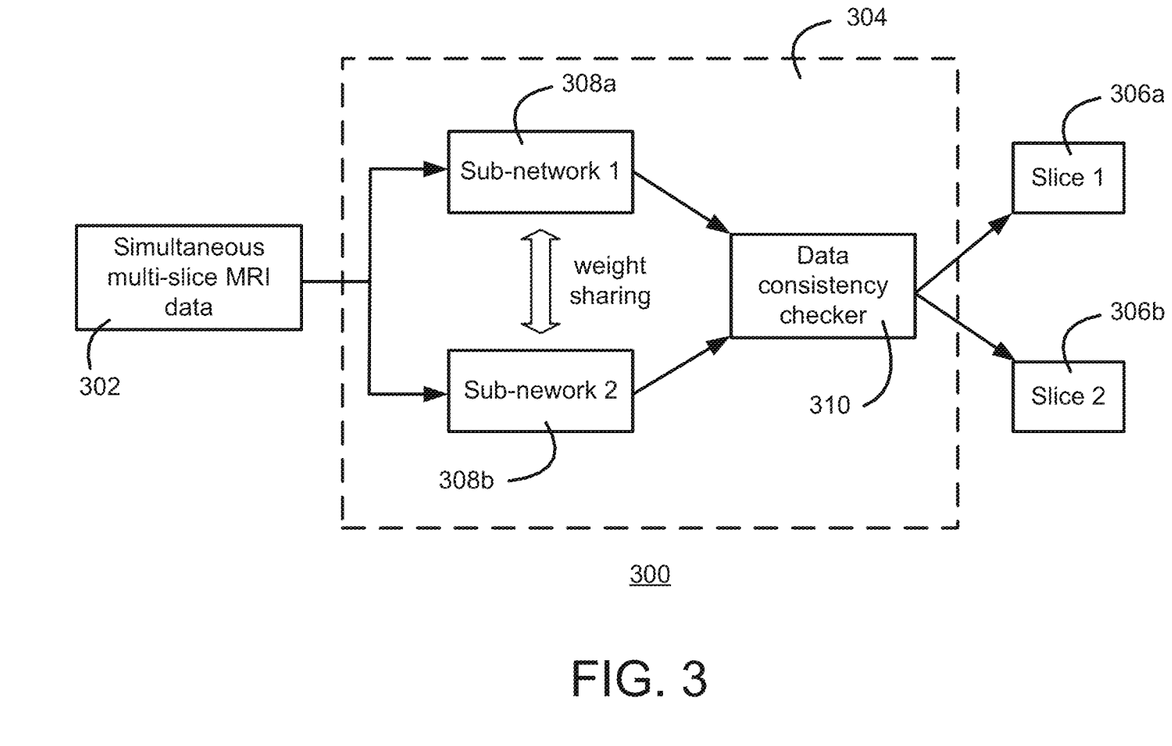
FIG. 3 is a block diagram illustrating an example implementation of a multi-slice MRI data processing system in accordance with one or more embodiments described herein.

FIG. 3 shows an example implementation of a multi-slice MRI data processing system 300 (e.g., the system 100 of FIG. 1) configured to process an SMS dataset 302 (e.g., the SMS dataset 102 of FIG. 1). As described herein, the SMS dataset 302 may comprise MRI data (e.g., under-sampled MRI data) associated with multiple MRI slices (e.g., two or more slices). The multiple MRI slices may be acquired, for example, using an SMS excitation technique and, as such, the MRI data associated with each of the multiple MRI slices may be entangled in the MRI dataset 302. The system 300 may include an artificial neural network 304 (e.g., the ANN 104 in FIG. 1) that may be pre-trained to receive the SMS dataset 302 and reconstruct respective MRI data (e.g., MRI images) for the multiple MRI slices based on the SMS dataset 302. The reconstructed MRI data for the slices may be disentangled (e.g., 306a for slice 1, 306b for slice 2, etc.) and may have a quality similar to that of a fully-sampled MRI image.

In examples, the ANN 304 may include multiple (e.g., two or more) sub-networks (e.g., 308a and 308b shown in FIG. 3) having identical or substantially similar structures (e.g., in terms of the number of layers, types of layers, number of feature maps or vectors generated by each network, etc.) and/or identical or substantially similar operating parameters (e.g., weights associated with the kernels or filters of each network). Each of the multiple sub-networks may be trained to process a corresponding MRI slice included in the SMS dataset 302 and, together, the multiple sub-networks may be capable of learning (e.g., identifying) the similarities and/or dissimilarities of the different MRI slices included in the SMS dataset 302 and denoise (e.g., remove artifacts from) the SMS dataset 302 based on the learned (e.g., identified) similarities and/or dissimilarities. The example in FIG. 3 shows that the sub-networks (e.g., 308a and 308b) may be configured to form a Siamese neural network, but those skilled in the art will appreciate that more than two sub-networks may be used to process the SMS dataset 302 (e.g., N sub-networks may be used respectively to process N slices, where N may be greater than two), and the sub-networks may share similar structures and/or operating parameters. Those skilled in the art will also appreciate that in some implementations the ANN 304 may include just one network (e.g., instead of the multiple sub-networks described herein) and the ANN may be trained to process the multiple MRI slices included in the SMS dataset 302 sequentially, learn (e.g., identify) the similarities and/or dissimilarities of the multiple MRI slices through the processing, and denoise (e.g., remove artifacts from) each MRI slice of the SMS dataset 302 based on the learned (e.g., identified) similarities and/or dissimilarities.

In examples, each of the multiple sub-networks or the single network described herein may include a convolutional neural network (CNN) configured to receive a respective input MRI image and extract features from the input image. Such an input MRI image may be a part of the multi-slice MRI dataset 302 or the input MRI image may be obtained (e.g., if the multi-slice MRI dataset 302 includes raw MRI data rather than MRI images) by applying inverse FFT to the k-space data included in the multi-slice MRI dataset 302. The CNN may include a plurality of layers such as one or more convolutional layers, one or more pooling layers, and/or one or more fully connected layers. Each of the convolutional layers may include a plurality of convolution kernels or filters configured to extract specific features from an input MRI image. The convolution operation may be followed by batch normalization and/or non-linear activation, and the features extracted by the convolutional layers (e.g., in the form of twin feature maps or feature vectors) may be down-sampled through the pooling layers and/or the fully connected layers (e.g., using a 2×2 window and a stride of 2) to reduce the redundancy and/or dimension of the features (e.g., by a factor of 2). In examples (e.g., when the input includes dynamic images), a recurrent convolutional neural network structure may be used to extract certain hidden states of the input using one or more convolutional layers and pass those hidden states through different image frames.

The respective feature maps or vectors generated by the CNNs may be used to determine the similarities (or dissimilarities) among the different slices of SMS dataset 302 and remove noises (e.g., artifacts caused by the other slice(s)) from each of the MRI slices based on the determined similarities or dissimilarities. For example, with respect to any one of the multiple MRI slices, the noise (e.g., artifacts) may correspond to MRI information introduced by one or more other MRI slices and such an impact may be mutual among the MRI slices since the slices may be acquired simultaneously. Thus, if a first MRI slice affects a second MRI slice at a certain spatial frequency, the first MRI slice may also be affected by the second MRI slice at the same spatial frequency. Therefore, the similarities among the multiple MRI slices may indicate a noise or artifact pattern, and by learning these similarities the CNNs may be able to remove the noise from each of the MRI slices.

In examples, the CNN associated with each sub-network 308a, 308b may further include one or more un-pooling layers and one or more transposed convolutional layers. Through the un-pooling layers, the CNN may up-sample the features extracted previously and further process the up-sampled feature representations through one or more transposed convolution operations (e.g., deconvolution operations), followed by one or more batch normalization operations, to derive one or more dense feature maps (e.g., which may be up-scaled by a factor of 2). The dense feature maps may then be used to generate MRI data that have the quality of a fully-sampled MRI dataset.

In examples, the ANN 304 may further include a data consistency (DC) checker 310 (e.g., as a layer of the ANN 304) that is configured to check and/or improve the fidelity of the MRI data predicted by the ANN 304. For example, the DC checker 310 may be configured to receive the MRI data produced by the Siamese network (e.g., denoised first and second intermediate MRI images respectively predicted by the sub-networks 308a and 308b based on the input), process the data (e.g., the first and second intermediate MRI images) to derive corresponding MRI (e.g., k-space data), and obtain respective MRI images (e.g., disentangled MRI images 306a and 306b) corresponding to the multiple slices of the SMS dataset 302 based on the derived MRI data (e.g., by applying an inverse Fourier transform such as an inverse FFT to the derived MRI data).

Various techniques may be used to derive the MRI data based on the estimates produced by the sub-networks 308a, 308b. As an example, denoting desired MRI data as s(k) (e.g., a desired SMS dataset), s(k) may be determined based on the following equation:

$$s(k)=f(s1(k),s2(k)) \qquad 1),$$

where k may present a readout line in the k-space, s1(k) and s2(k) may represent two MRI slices, and f may represent a function for combining the two MRI slices to obtain s(k). The function f may take the following form:

$$f(a,b)=u*a+v*b \qquad 2),$$

where the values of u and v may be manipulated (e.g., adjusted) to emulate modulations that are applied to MRI slices a, b. For instance, for all the even readout lines (e.g., where k is an even number), the values of u and v may be set to u=1, v=1 such that s(k)=s1(k)+s2(k), and for all the odd readout lines (e.g., where k is an odd number), the values of u and v may be set to u=1, v=-1 such that s(k)=s1(k)-s2(k). On the other hand, if the MRI images I1(x) and I2(x) (e.g., intermediate MRI images) predicted by the sub-networks 301a and 308b are stacked together along a direction z, the corresponding image space may be represented by I(x,z)=[I1(x), I2(x)]. Applying a Fourier transform (e.g., a fast Fourier transform) along the z direction, the following may be derived (e.g., based on properties of the Fourier transform):

$$J(x,kz)=\text{FFTz}(I(x,z))=[I1(x)+I2(x),I1(x)-I2(x)] \qquad 3),$$

where J(x, kz=0) may be equal to I1(x)+I2(x) and J(x, kz=1) may be equal to I1(x)-I2(x). Comparing this to Equations 1) and 2) shown above, s(k)=s1(k)+s2(k) may correspond to kz=0, s(k)=s1(k)-s2(k) may correspond to kz=1, and the predictions (e.g., MRI images) made by the sub-networks 308a, 308b may be converted to MRI data based on, for example, s(k, kz)=[s1(k)+s2(k), s1(k)-s2(k)]. Using the MRI data thus obtained, respective reconstructed MRI images (e.g., 306a and 306b) corresponding to the multiple slices may be obtained, for example, by applying an inverse FFT to the MRI data, as illustrated by Equation 4) below:

$$\text{iFFT}\_k\_kz(s(k,kz))=I(x,z)=[I1(x),I2(x)] \qquad 4)$$

In examples, the DC checker 310 may be configured to compare the denoised MRI data (e.g., obtained using the techniques described herein) to the MRI data actually acquired (e.g., represented by the SMS dataset 302) to ensure data consistency or fidelity. For example, the DC checker 310 may be configured to compensate for an estimation bias introduced by the ANN 304 by replacing one or more portions of the estimated MRI data with corresponding portions of the SMS dataset 302 (e.g., where data is actually acquired). Such fidelity-compensated MRI data may then be transformed to the image space (e.g., via inverse FFT) to obtain fidelity-compensated MRI images for the multiple slices.

The techniques described herein may be advantageous over other deep learning based techniques for processing SMS data. One of the reasons may be that, in an SMS dataset, the slices acquired may be separated by a greater distance in space (e.g., to avoid slice interference) and, as such, the other deep-learning based techniques such as those utilizing 3D convolutional kernels may not be able to produce satisfactory results. In contrast, since there may still be correlations between the slices (e.g., the slices may all be related to a same physiological process such as cardiac contraction), the neural network structure described herein may be suitable for learning the similarities or dissimilarities among the slices and removing artifacts from the SMS based on the determined similarities or dissimilarities.

It should be noted that even though examples may be described herein in the context of two MRI slices, two MRI datasets, or two sub-networks, those skilled in the art will appreciate that the techniques disclosed herein may also be applicable to more than two (e.g., three or more) MRI slices, more than two MRI datasets, or more than two subnetworks.

In examples, the reconstruction results obtained using the ANN 304 may be further improved by exploiting characteristics of the coils used to acquire the multi-slice MRI dataset 302. These characteristics may include, for example, correlations of the multiple coils that may be indicated by one or more coil sensitivity maps associated with the coils. These coil sensitivity maps may be estimated, e.g., from a reference scan or based on one or more calibration regions of the multi-slice MRI dataset 302. The coil sensitivity maps may include, for example, a first coil sensitivity map associated with a first set of one or more coils that is used to acquire information associated with a first MRI slice and a second coil sensitivity map associated with a second set of one or more coils that is used to acquire information associated with a second MRI slice (e.g., the first and second sets of coils may overlap (e.g., include the same coil(s)). Once obtained, the coil sensitivity maps associated with the coils may be applied (e.g., by the ANN 304 and/or the DC checker 310) along with the Fourier transforms to reconstruct the multi-slice MRI data. For instance, MRI data (e.g., MRI images) associated with the multiple coils may be multiplied with corresponding complex conjugates of the coil sensitivity maps and then summed together to obtain coil-combined MRI images that may then be provided to the sub-networks 308a, 308b for denoising. The coil-combined MRI data may be re-distributed to the multiple coils, for example, by multiplying the combined data with the coil sensitivity map of each set of coils. The re-distributed multi-coil images may then be transformed to k-space to perform fidelity checking and/or compensation, as described herein. A coil compression layer (e.g., as a part of the ANN 304) may be utilized to compress the MRI data among the coil directions.

Figure 4:
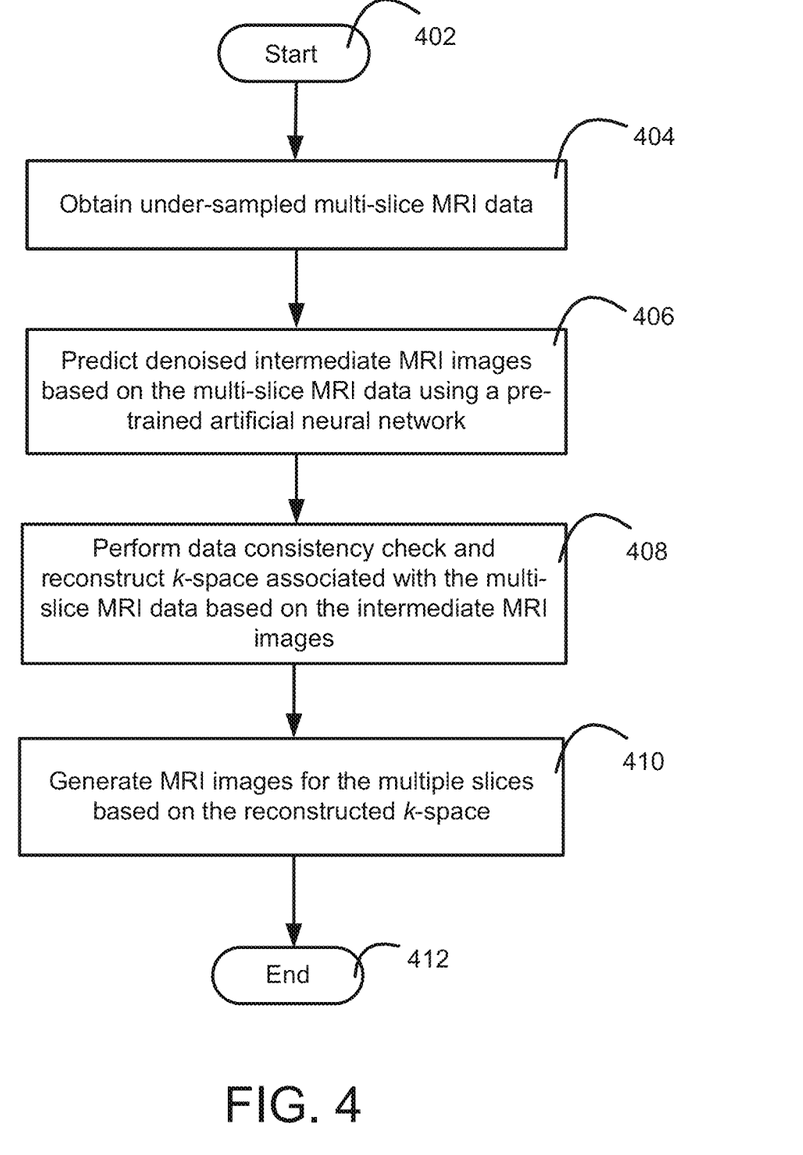
FIG. 4 is a flow diagram illustrating example operations that may be performed by a multi-slice MRI data processing system in accordance with one or more embodiments described herein.

FIG. 4 is a flow diagram illustrating example operations that may be performed by a multi-slice MRI data processing system (e.g., the system 100 of FIG. 1 and/or the system 300 of FIG. 3) in accordance with one or more embodiments described herein. As shown, the operations may start at 402 and at 404 the MRI data processing system may receive a multi-slice MRI dataset such as an SMS dataset that comprises under-sampled MRI data (e.g., k-space data or MRI images) associated with multiple MRI slices of an anatomical structure. At 406, the MRI data processing system may process the multi-slice MRI data using a pre-trained artificial neural network (e.g., the Siamese network shown in FIG. 3) to remove noises (e.g., artifacts) from the input MRI data. At 408, the denoised MRI data (e.g., denoised intermediate MRI images estimated by the artificial neural network) may be further processed by a data consistency component (e.g., the DC checker 310 of FIG. 3) during which fidelity of the estimated MRI data may be verified and/or improved, and MRI data corresponding to the input multi-slice MRI dataset may be reconstructed (e.g., by converting the estimated intermediate MRI images into the MRI data via Fourier transforms). Based on the reconstructed MRI data, the MRI data processing system may at 410 generate MRI images for the multiple slices included in the input MRI dataset by applying inverse FFT to the reconstructed MRI data. The MRI images thus generated may be disentangled and have a higher quality (e.g., similar to that of a fully-sampled MRI image) when compared to the input multi-slice MRI dataset. The operations of the multi-slice MRI data processing system may then end at 412.

Figure 5:
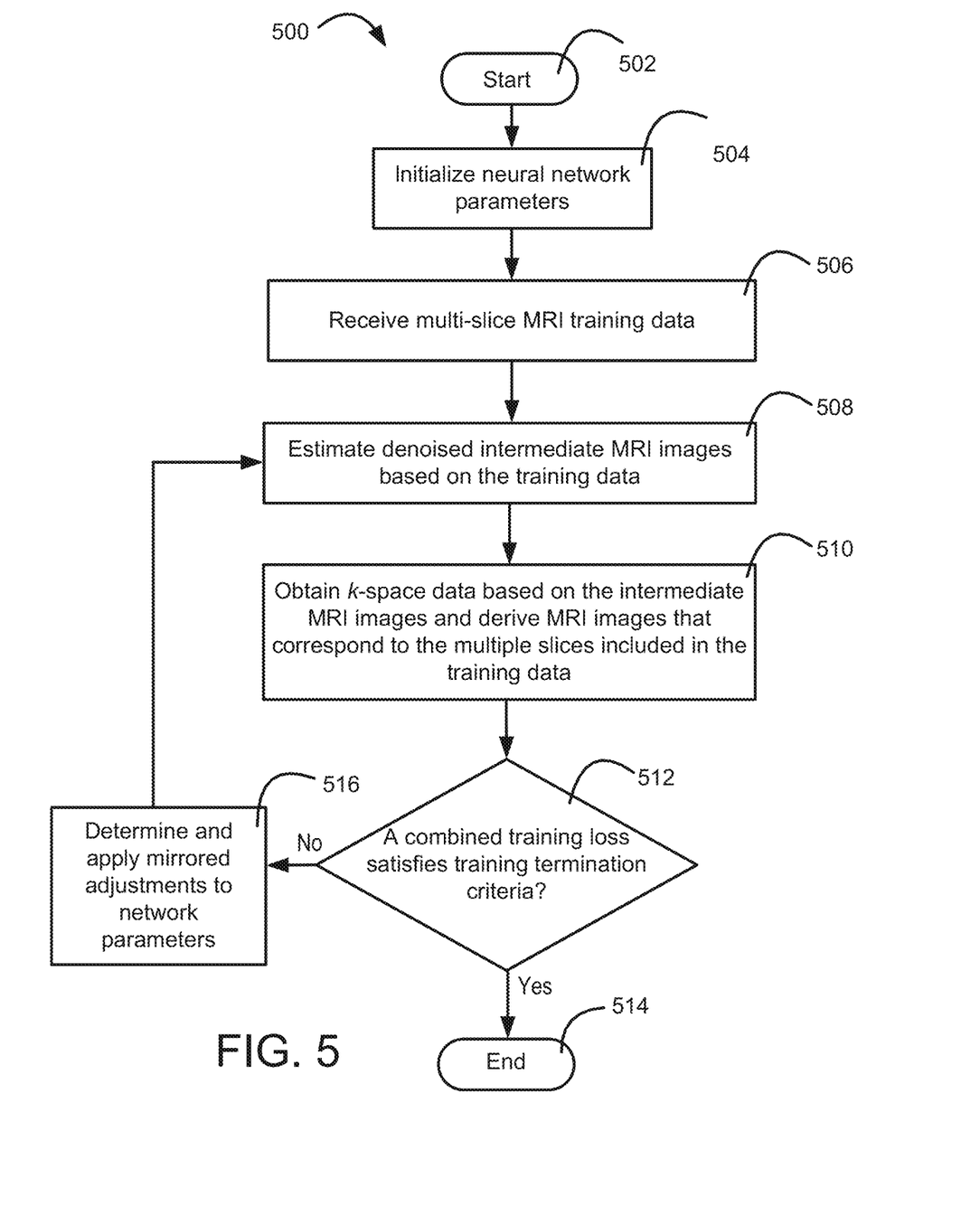
FIG. 5 is flow diagram illustrating an example process for training a neural network to perform the image reconstruction tasks described herein.

FIG. 5 illustrates an example process 500 for training a neural network (e.g., an instance of the ANN 104 of FIG. 1 and/or ANN 304 of FIG. 3) to perform the multi-slice MRI data processing operations described herein. The training may be performed using data collected from practical MRI procedures (e.g., under-sampled multi-slice MRI data acquired using an SMS technique), and/or computer-simulated or computer-augmented MRI data. For example, fully-sampled multi-slice 2D or 3D MRI images collected from real MRI procedures may be used as a starting point for simulating the training data. Selected slices may be extracted from the real MRI data with sufficient slice distance and modulations of the slices may be emulated by adding phase modulation terms to each slice. Data associated with the multiple slices may be combined (e.g., summed) to obtain an SMS dataset directly in the image space, or the multiple slice may be transformed into the k-space first and then combined (e.g., summed) to obtain the SMS dataset. Additional in-plane under-sampling may be combined with through-plane under-sampling during the data simulation process.

As shown in FIG. 5, the training process 500 may start at 502 and at 504 parameters of the neural network (e.g., weights associated with various filters or kernels of the neural network) may be initialized. The parameters may be initialized, for example, based on samples collected from one or more probability distributions or parameter values of another neural network having a similar architecture. At 506, the neural network may receive a set of under-sampled multi-slice MRI training data (e.g., SMS data) that comprise entangled MRI information associated with multiple MRI slices. The training data may be provided in the format of an under-sampled MRI image or under-sampled k-space data (e.g., raw MRI data). In the latter case, the under-sampled k-space data may be converted into an MRI image, for example, via Fourier transforms. As described herein, the neural network may comprise multiple structurally identical sub-networks (e.g., the sub-networks 308a, 308b shown in FIG. 3) each configured to process the training data associated with a respective MRI slice, or the neural network may comprise just one network configured to process the training data associated with the multiple MRI slices sequentially.

At 508, the neural network may process the training data associated with the multiple MRI slices and generate respective intermediate MRI images in which all or a subset of the artifacts (e.g., noises) present in the training data may be removed. At 510, the intermediate MRI images generated by the neural network may be combined and/or converted (e.g., by a data consistency component of the neural network such as the DC checker 310 of FIG. 3) to obtain reconstructed MRI data corresponding to the multiple slices included in the input training dataset. The reconstructed MRI data may then be used to derive respective estimated MRI images (e.g., denoised and disentangled MRI images) for the multiple slices. At 512, a combined training loss may be determined by jointly considering the estimated MRI images associated with the multiple slices. For example, the combined training loss may be determined based on a triplet loss or a contrastive loss associated with the estimated MRI images of the multiple MRI slices. In examples, the combined training loss may be determined based on an average of the respective training losses associated with the multiple MRI slices, while each of the respective training losses (e.g., corresponding to an individual MRI slice) may be determined by comparing the estimated MRI image for the individual MRI slice with a corresponding ground truth MRI image. Various suitable loss functions including, for example, those based on mean square errors, an L1 norm, an L2 norm, a structural similarity index (SSIM), etc. may be used to calculate the losses described herein. Once determined, the combined training loss (e.g., derived by jointly considering the estimated MRI images of the multiple slices) may be used to determine whether one or more training termination criteria have been satisfied. For example, it may be determined that the training termination criteria are satisfied if the combined training loss is below a predetermined threshold, if changes in the respective combined training losses between two training iterations (e.g., between consecutive training iterations) are below a predetermined threshold, etc. If the determination at 512 is that the training termination criteria are satisfied, the training process 500 may end at 514. If the determination at 512 is that the training termination criteria are not satisfied, the neural network may at 516 adjust its parameters by backpropagating the training loss (e.g., based on a gradient descent associated with the training loss) through the neural network. In examples such as when the neural network includes multiple structurally similar sub-networks, mirrored adjustments may be applied to the respective parameters of the sub-networks (e.g., weights associated with the filters or kernels of the sub-networks) before the training operations return to 508. This way, parameter sharing may be accomplished among the multiple sub-networks.

For simplicity of explanation, the training steps are depicted and described herein with a specific order. It should be appreciated, however, that the training operations may occur in various orders, concurrently, and/or with other operations not presented or described herein. Furthermore, it should be noted that not all operations that may be included in the training process the are depicted and described herein, and not all illustrated operations are required to be performed.

Figure 6:
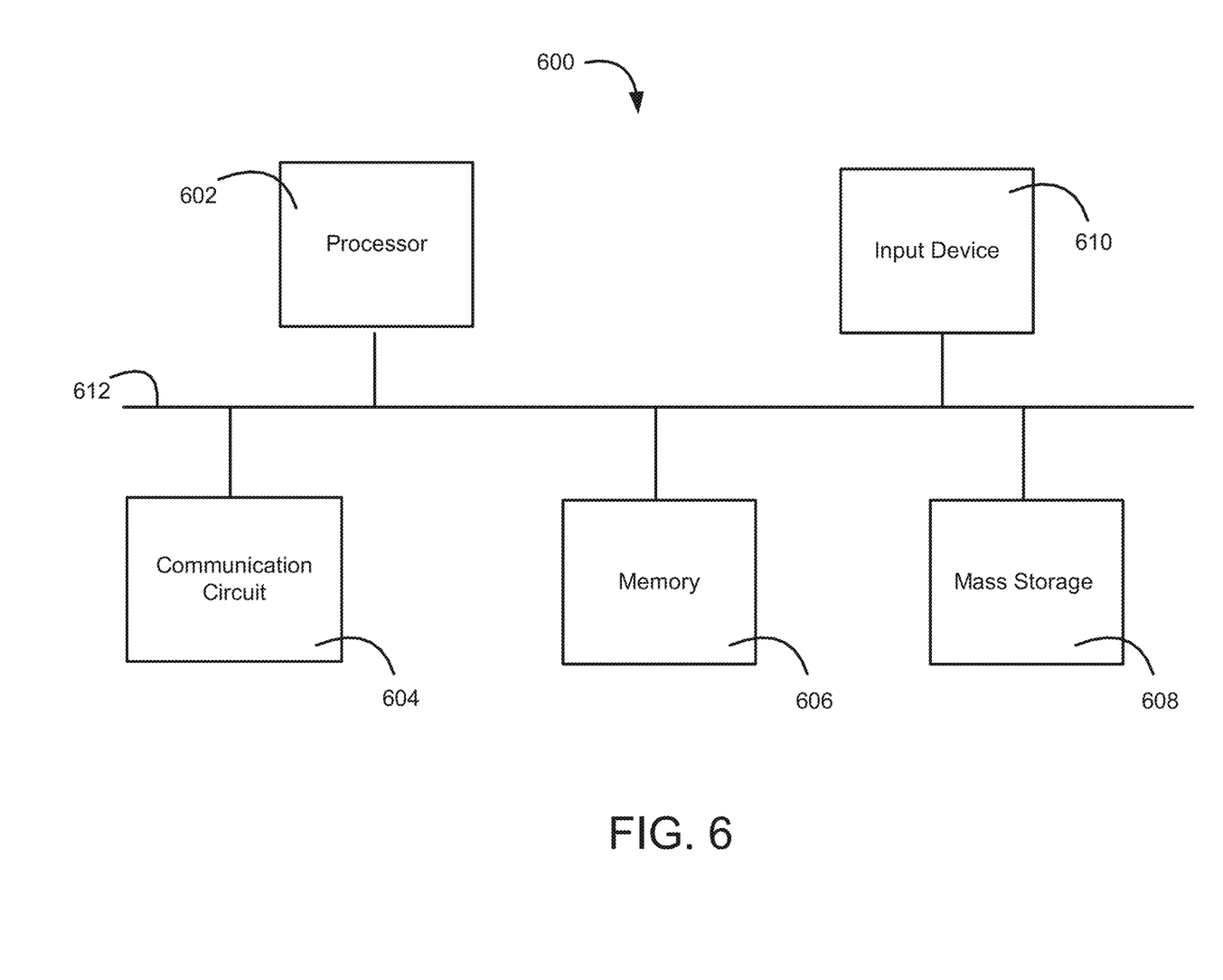
FIG. 6 is a block diagram illustrating example components of an apparatus that may be used to perform the image reconstruction tasks described herein.

The systems, methods, and/or instrumentalities described herein may be implemented using one or more processors, one or more storage devices, and/or other suitable accessory devices such as display devices, communication devices, input/output devices, etc. FIG. 6 is a block diagram illustrating an example apparatus 600 that may be configured to perform the multi-slice MRI data processing tasks described herein. As shown, the apparatus 600 may include a processor (e.g., one or more processors) 602, which may be a central processing unit (CPU), a graphics processing unit (GPU), a microcontroller, a reduced instruction set computer (RISC) processor, application specific integrated circuits (ASICs), an application-specific instruction-set processor (ASIP), a physics processing unit (PPU), a digital signal processor (DSP), a field programmable gate array (FPGA), or any other circuit or processor capable of executing the functions described herein. The apparatus 600 may further include a communication circuit 604, a memory 606, a mass storage device 608, an input device 610, and/or a communication link 612 (e.g., a communication bus) over which the one or more components shown in the figure may exchange information.

The communication circuit 604 may be configured to transmit and receive information utilizing one or more communication protocols (e.g., TCP/IP) and one or more communication networks including a local area network (LAN), a wide area network (WAN), the Internet, a wireless data network (e.g., a Wi-Fi, 3G, 4G/LTE, or 5G network). The memory 606 may include a storage medium (e.g., a non-transitory storage medium) configured to store machine-readable instructions that, when executed, cause the processor 602 to perform one or more of the functions described herein. Examples of the machine-readable medium may include volatile or non-volatile memory including but not limited to semiconductor memory (e.g., electrically programmable read-only memory (EPROM), electrically erasable programmable read-only memory (EEPROM)), flash memory, and/or the like. The mass storage device 608 may include one or more magnetic disks such as one or more internal hard disks, one or more removable disks, one or more magneto-optical disks, one or more CD-ROM or DVD-ROM disks, etc., on which instructions and/or data may be stored to facilitate the operation of the processor 602. The input device 610 may include a keyboard, a mouse, a voice-controlled input device, a touch sensitive input device (e.g., a touch screen), and/or the like for receiving user inputs to the apparatus 600.

It should be noted that the apparatus 600 may operate as a standalone device or may be connected (e.g., networked or clustered) with other computation devices to perform the functions described herein. And even though only one instance of each component is shown in FIG. 6, a skilled person in the art will understand that the apparatus 600 may include multiple instances of one or more of the components shown in the figure.

While this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "analyzing," "determining," "enabling," "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. A method for reconstructing magnetic resonance imaging (MRI) images, the method comprising:
   obtaining a simultaneous multi-slice (SMS) dataset, wherein the SMS dataset comprises first under-sampled MRI data associated with a first MRI slice of an organ and second under-sampled MRI data associated with a second MRI slice of the organ, the first MRI slice and the second MRI slice simultaneously acquired from an MRI procedure; and generating, using an artificial neural network (ANN), a first reconstructed MRI image of the organ corresponding to the first MRI slice and a second reconstructed MRI image of the organ corresponding to the second MRI slice, wherein the ANN is trained for generating the first reconstructed MRI image and the second reconstructed MRI image, and the training comprises:

processing first under-sampled MRI training data of an SMS training dataset through an instance of the ANN to obtain a first estimated MRI image, the first under-sampled MRI training data corresponding to a first MRI slice of the SMS training dataset;

processing second under-sampled MRI training data of the SMS training dataset through the instance of the ANN to obtain a second estimated MRI image, the second under-sampled MRI training data corresponding to a second MRI slice of the SMS training dataset;

determining a combined training loss by jointly considering a first training loss associated with the first estimated MRI image and a second training loss associated with the second estimated MRI image; and adjusting parameters of the instance of the ANN based on a gradient descent of the combined training loss.

2. The method of claim 1, wherein the first under-sampled MRI data includes first artifacts that are associated with the second under-sampled MRI data, wherein the second under-sampled MRI data includes second artifacts that are associated with the first under-sampled MRI data, and wherein the first reconstructed MRI image and the second reconstructed MRI image are substantially free of the first artifacts and the second artifacts, respectively.

3. The method of claim 1, wherein the first training loss is determined based on the first estimated MRI image and a corresponding first ground truth MRI image, the second training loss is determined based on the second estimated MRI image and a corresponding second ground truth MRI image, and the combined training loss is determined based on an average of the first loss and the second loss.

4. The method of claim 1, wherein the ANN comprises a first sub-network and a second sub-network, the first sub-network configured to process the first under-sampled MRI data, the second sub-network configured to process the second under-sampled MRI data, and wherein the first sub-network and the second sub-network share substantially similar structures and operating parameters.

5. The method of claim 4, wherein, during the training of the ANN, the first sub-network of the instance of the ANN is configured to process the first under-sampled MRI training data, the second sub-network of the instance of the ANN is configured to process the second under-sampled MRI training data, and adjusting the parameters of the instance of the ANN comprises applying mirrored updates to respective parameters of the first sub-network and the second sub-network.

6. The method of claim 1, wherein the first under-sampled MRI data associated with the first MRI slice comprises a first under-sampled MRI image or first under-sampled k-space data, and the second under-sampled MRI data associated with the second MRI slice comprises a second under-sampled MRI image or second under-sampled k-space data.

7. The method of claim 1, wherein the ANN further comprises a data consistency (DC) component configured to estimate k-space data based on a first intermediate MRI image generated by the ANN using the first under-sampled MRI data and a second intermediate MRI image generated by the ANN using the second under-sampled MRI data, and wherein the first reconstructed MRI image and the second reconstructed MRI image are generated by applying an inverse Fourier transform to the estimated k-space data.

8. The method of claim 7, further comprising, prior to applying the inverse Fourier transform to the estimated k-space data, replacing at least a portion of the estimated k-space data with a corresponding portion of the SMS dataset.

9. The method of claim 7, wherein the first under-sampled MRI data comprised in the SMS dataset comprises MRI data acquired using a first set of one or more coils, the second under-sampled MRI data comprised in the SMS dataset comprises MRI data acquired using a second set of one or more coils, and wherein the method further comprises determining respective coil sensitivity maps associated with the first set of one or more coils and the second set of one or more coils.

10. The method of claim 9, wherein the k-space data is estimated further based on the respective coil sensitivity maps associated with the first set of one or more coils and the second set of one or more coils.

11. An apparatus, comprising:
one or more processors configured to:
obtain a simultaneous multi-slice (SMS) dataset, wherein the SMS dataset comprises first under-sampled magnetic resonance imaging (MRI) data associated with a first MRI slice of an organ and second under-sampled MRI data associated with a second MRI slice of the organ, the first MRI slice and the second MRI slice simultaneously acquired from an MRI procedure; and generate, using an artificial neural network (ANN), a first reconstructed MRI image of the organ corresponding to the first MRI slice and a second reconstructed MRI image of the organ corresponding to the second MRI slice, wherein the ANN is trained for generating the first reconstructed MRI image and the second reconstructed MRI image, and the training comprises:

processing first under-sampled MRI training data of an SMS training dataset through an instance of the ANN to obtain a first estimated MRI image, the first under-sampled MRI training data corresponding to a first MRI slice of the SMS training dataset;

processing second under-sampled MRI training data of the SMS training dataset through the instance of the ANN to obtain a second estimated MRI image, the second under-sampled MRI training data corresponding to a second MRI slice of the SMS training dataset;

determining a combined training loss by jointly considering a first training loss associated with the first estimated MRI image and a second training loss associated with the second estimated MRI image; and adjusting parameters of the instance of the ANN based on a gradient descent of the combined training loss.

12. The apparatus of claim 11, wherein the first under-sampled MRI data includes first artifacts associated with the second under-sampled MRI data, the second under-sampled MRI data includes second artifacts associated with the first under-sampled MRI data, and wherein the first reconstructed MRI image and the second reconstructed MRI image are substantially free of the first artifacts and the second artifacts, respectively.

13. The apparatus of claim 11, wherein the first training loss is determined based on the first estimated MRI image and a corresponding first ground truth MRI image, the second training loss is determined based on the second estimated MRI image and a corresponding second ground truth MRI image, and the combined training loss is determined based on an average of the first loss and the second loss.

14. The apparatus of claim 11, wherein the ANN comprises a first sub-network and a second sub-network, the first sub-network configured to process the first under-sampled MRI data, the second sub-network configured to process the second under-sampled MRI data, and wherein the first sub-network and the second sub-network share substantially similar structures and operating parameters.

15. The apparatus of claim 14, wherein, during the training of the ANN, the first sub-network of the instance of the ANN is configured to process the first under-sampled MRI training data, the second sub-network of the instance of the ANN is configured to process the second under-sampled MRI training data, and wherein adjusting the parameters of the instance of the ANN comprises applying mirrored updates to respective parameters of the first sub-network and the second sub-network.

16. The apparatus of claim 11, wherein the first under-sampled MRI data associated with the first MRI slice comprises a first under-sampled MRI image or first under-sampled k-space data, and the second under-sampled MRI data associated with the second MRI slice comprises a second under-sampled MRI image or second under-sampled k-space data.

17. The apparatus of claim 11, wherein the ANN further comprises a data consistency (DC) component configured to estimate k-space data based on a first intermediate MRI image generated by the ANN using the first under-sampled MRI data and a second intermediate MRI image generated by the ANN using the second under-sampled MRI data, and wherein the first reconstructed MRI image and the second reconstructed MRI image are generated by applying an inverse Fourier transform to the estimated k-space data.

18. The apparatus of claim 17, wherein, prior to applying the inverse Fourier transform to the estimated k-space data, at least a portion of the estimated k-space data is replaced with a corresponding portion of the SMS dataset.

19. The apparatus of claim 17, wherein the first under-sampled MRI data comprised in the SMS dataset comprises MRI data acquired using a first set of one or more coils, the second under-sampled MRI data comprised in the SMS dataset comprises MRI data acquired using a second set of one or more coils, and wherein the one or more processors are further configured to determine respective coil sensitivity maps associated with the first set of one or more coils and the second set of one or more coils.

20. The apparatus claim 19, wherein the k-space data is estimated further based on the respective coil sensitivity maps associated with the first set of one or more coils and the second set of one or more coils.

* * * * *